United States Patent
Larsen et al.

(10) Patent No.: US 7,182,085 B1
(45) Date of Patent: Feb. 27, 2007

(54) PRESSURE RELIEVING DRESSING

(75) Inventors: Truels Sterm Larsen, Copenhagen N (DK); Henrik Olsen, Ballerup (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/926,293

(22) PCT Filed: Apr. 6, 2000

(86) PCT No.: PCT/DK00/00168

§ 371 (c)(1),
(2), (4) Date: Oct. 9, 2001

(87) PCT Pub. No.: WO00/61046

PCT Pub. Date: Oct. 19, 2001

(30) Foreign Application Priority Data

Apr. 7, 1999 (DK) ................ 1999 00463
Apr. 7, 1999 (DK) ................ 1999 00464

(51) Int. Cl.
*A61F 13/00* (2006.01)

(52) U.S. Cl. .......................... 128/846; 602/41

(58) Field of Classification Search ........... 128/846, 128/887–889, 893–894, 877, 878, 879; 442/877; 424/878, 879; 602/41–48, 56

See application file for complete search history.

(56) References Cited

U.S. PATENT DOCUMENTS

| | | | | |
|---|---|---|---|---|
| 3,670,731 A | 6/1972 | Harmon | ...... | 128/284 |
| 3,824,996 A | 7/1974 | Carlisle | ...... | 128/156 |
| 4,776,331 A | 10/1988 | Simjian | ...... | 128/169 |
| 5,176,663 A * | 1/1993 | Svedman | ...... | 604/305 |
| 5,181,905 A * | 1/1993 | Flam | ...... | 602/41 |
| 5,376,067 A * | 12/1994 | Daneshvar | ...... | 602/13 |
| 5,488,786 A | 2/1996 | Ratay | ...... | 36/44 |
| 5,507,721 A * | 4/1996 | Shippert | ...... | 602/46 |
| 5,642,096 A | 6/1997 | Leyerer et al. | ...... | 340/573 |
| 5,891,074 A * | 4/1999 | Cesarczyk | ...... | 602/42 |
| 5,939,339 A * | 8/1999 | Delmore | ...... | 602/44 |
| 6,168,800 B1 * | 1/2001 | Dobos | ...... | 424/405 |
| 6,384,293 B1 * | 5/2002 | Marcussen | ...... | 602/41 |

FOREIGN PATENT DOCUMENTS

| | | | |
|---|---|---|---|
| DE | 2202703 | * | 2/1972 |
| DE | 35 39 533 | | 5/1987 |
| EP | 0 164 319 | | 12/1985 |
| EP | 0 430 608 | | 6/1991 |
| GB | 842847 | | 7/1960 |
| WO | 90/09746 | | 9/1990 |
| WO | 91/01706 | | 2/1991 |
| WO | 93/01777 | | 2/1993 |
| WO | 99/01166 | | 1/1999 |

* cited by examiner

*Primary Examiner*—Michael A. Brown
(74) *Attorney, Agent, or Firm*—Jacobson Holman PLLC

(57) ABSTRACT

A pressure relieving dressing comprising an absorbing element and a substantially non-absorbing pressure distributing element, in which the absorbent element constitutes a part of a proximal skin contacting surface, said absorbing element being encircled by the pressure distributing element or being situated at the border of the pressure distributing element constituting the remaining part of the surface of the dressing to be in contact with the skin rendering it possible to obtain an effective and durable dressing suitable for both wound healing and prophylaxis of pressure ulcers.

23 Claims, 4 Drawing Sheets

PRESSURE RELIEVING DRESSING

This is a nationalization of PCT/DK00/00168 filed Apr. 6, 2000 and published in English.

FIELD OF THE INVENTION

The present invention relates to a pressure relieving dressing used for prophylaxis or treatment of ulcers as well as for protection of fragile skin.

BACKGROUND OF THE INVENTION

Many people, especially diabetics, who suffers from long term complications such as ischeamia and neuropathy or patients confined to their bed are known to develop ulcers on foot, hip or sacrum. Foot ulcers are usually located on the planter or on the side or dorsum of the foot. Foot ulcers are induced by changes in bone structure, which can lead to protruding prominences and reduced thickness of the subcutaneous layer that ensures distribution and relief of the pressure applied to the foot.

The development of foot ulcers are i.e. dependent on a combination of etiology and the induction of pressure. There are essentially two mechanical inducers for pressure sore development, the stress of permanent (static) pressure and the stress of short term (dynamic) pressure.

The permanent or static pressure is when exertion of pressure over a long period (hours typically) is leading to the risk of collapse of veins and arteries. The collapse of these blood vessels may lead to ischemia e.g. lack of oxygen and nutrition and a build up of waste materials. These events may eventually lead to development of ulcers. The tendency is the longer period of pressure induction, the lower pressure is critical and may cause damage.

Short term or dynamic pressure impact is in the form of repetitive mechanical stress. This occurs e.g. when walking, where a typical pre-stage to ulceration is callus build-up. This type of ulceration may be compared to benign sanguinous blister formation. Critical pressure level of this type of pressure impact is much higher than in the case of a long time pressure load.

Dressings designed to manage wound healing and exudate are well known in the art. However, they do not take into account the effects of the pressure stress.

From International Patent application No. WO 91/01706 A1 (Smith & Nephew) is known a polymeric foam absorbent dressing for exudate handling in wound healing. No pressure relief/distribution properties are mentioned. This dressing comprises a foam material all over the surface. Since this open cell foam is designed to allow transportation of exudate, it has inadequate strength towards pressure, and will be compressed or collapse when worn on a foot.

WO 99/01166 A1 (Coloplast A/S) discloses a non-fibrous polysaccharide wound dressing capable of handling wound exudate by gelling properties. This material is very soft and gentle towards the ulcer. However, it has inadequate strength towards mechanical pressure and will collapse if pressure is applied.

Examples of pressure reducing/distributing/shock-lowering orthopaedic materials and products are also known:

In international Patent application No. WO 90/09746 A1 (Bernard, M.) is disclosed a composite inner sole for sports shoes, comprising a shock absorbing layer. No wound healing or exudate absorbing properties are mentioned.

U.S. Pat. No. 5,488,786 (Ratay, E. J.) discloses a highly resilient insole, designed to cover the hole sole of the shoe i.e. the whole plantar surface of the foot. No wound healing or exudate absorbing properties are mentioned.

Only few examples of a combining the two said properties are known:

From DE patent application No. 35 39 533 (Liedtke) is known a foam dressing. The dressing comprises a foam body, the non-skin-contacting surface optionally being covered with a film and the outer periphery of the skin-contacting edge covered with an adhesive. The foam serves both as a pressure reducing and distributing element and as an absorbent element. Between the adhesive-covered edge and the non-adhesive central part is a groove in the foam, as well as more grooves or indentations may appear in the central part. These grooves are made to enhance the flexibility of the dressing. The dressing is made of a single piece of foam, and the only barriers to control the wound exudate is the top film and the adhesive, leaving a severe risk of maceration when used on exuding wounds. In one embodiment of the invention, the dressing comprises a slit in the foam defining a lid to be opened and an absorbing pad may be inserted over the wound. However, this construction with a slit may give rise to problems with leakage.

GB patent No. 842 847 (Scholl) discloses a corn dressing, comprising a foam ring, serving as a pressure distributing part and a thinner central part with a napped inner side having a shock absorbing/cushioning effect. In the cavity between the central part and the skin/treated area a pad with medication may be placed. The reference is silent with respect to wound treatment as well as use of absorber, on the contrary, the device is donating medication to the treated site.

International Patent application No. WO 93/01777 A1 (Malloul, L.) discloses a dressing for sutured wounds. Said dressing has a foamed shock-absorbing element or cushion layer on both sides of the wound, protecting the wound from impact or pressure, and an area spaced apart from the wound with a pad right over the wound. The dressing only copes with dynamic pressure in the form of sudden impacts, and is silent with respect to static pressure.

European Patent No. EP 0 164 319 (Coloplast A/S) discloses a wound dressing of the hydrocolloid type with a pressure relief system of foam. The pressure is distributed through the foam in order to relieve the pressure on the ulcer. The dressing offers a possibility to adapt a specific relief area corresponding to the size of the ulcer, rendering it possible to transfer the pressure from the wound site to the surrounding healthy tissue. The pressure relief is described as having static pressure relieving properties, not dynamic pressure/shock relieving properties.

Diabetic patients are often suffering from neuropathy, rendering their sensibility skills to be greatly diminished or they may even suffer from a complete loss of feelings in the lower extremities, and especially in the feet. The patient will often fail to notice or be aware when individual points of a foot are subjected to severe constant pressure or repetitive stress, for example during long periods of standing or by use of badly fitting shoes, inducing the development of an pressure sore. Since metabolism is disturbed and blood circulation already can be reduced in diabetes patients, healing of such sores is most difficult.

Attempts have been made to prevent the development of pressure sores and ulcers in a patient who might not be able to recognise presence of severe sore inducing condition.

Dressings with different kinds of indicators are known, e.g. from European Patent application No. 430 608 (E. R. Squibb & Sons, Inc.), which discloses a wound dressing comprising a temperature sensing liquid crystal tape, affixed to the backing layer. A temperature change may indicate a change in wound condition. In the reference is also mentioned the possibility of a pressure indicator in the form of a piezoelectric element.

U.S. Pat. No. 5,642,096 (Paromed Medizintechnik GmbH) discloses a device for prevention of ulcers on the feet of diabetic patients. The device includes a pressure and temperature sensor in the form of a piezoelectric element carried in the innersole of the shoe. The patient is warned by a signal, e.g. a buzz if the pressure reaches a critical level. The device is constricted to the innersole of the shoe, and does not cope with detecting impacts to other body parts e.g. the side of the foot or on hips or sacrum, and it is also technically complicated and expensive.

Until now a dressing being capable of both handling wound exudate and at the same time relieving both static and dynamic pressure has not been disclosed.

It has now surprisingly been found that the above mentioned problem can be overcome by combining a shock-absorbing material with a moisture-absorbing material rendering it possible to obtain an effective and durable dressing suitable for both wound healing and prophylaxis of pressure ulcers as well as for protection of fragile skin.

BRIEF DESCRIPTION OF THE INVENTION

The present invention relates to a pressure relieving dressing comprising an absorbent element and a substantially non-absorbing pressure distributing element.

BRIEF DESCRIPTION OF THE DRAWINGS

The invention is explained more in detail with reference to the drawings in which.

DETAILED DESCRIPTION OF THE INVENTION

Figure 1:
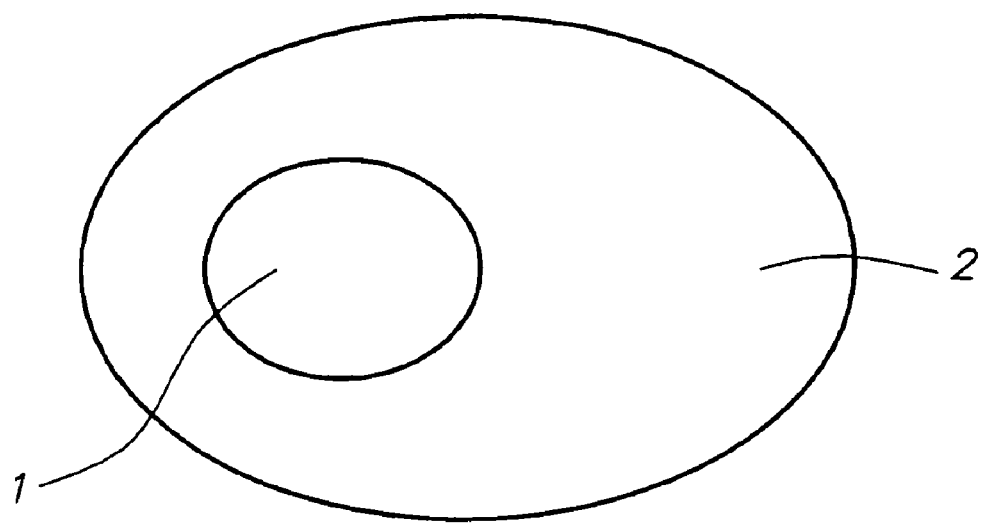
FIG. 1 shows a top view of an embodiment of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention relates to a pressure relieving dressing comprising an absorbent element and a substantially non-absorbing pressure distributing element, wherein the absorbent element constitute part of a proximal skin contacting surface, said absorbent element being encircled by the pressure distributing element constituting the remaining part of the surface of the dressing to be in contact with the skin, characterised in that the absorbent element is situated eccentrically with respect to the pressure distributing element.

The absorbent element may be situated at the border of the pressure distributing element.

In order to prevent the development of ulcers and/or enhance the healing of ulcers a combination of an absorbent element and a pressure distributing and pressure shock-absorbing element has been shown to be advantageous. The absorbent element is able to handle exudates from a wound and provide the optimal environment for wound healing, while the pressure distributing element will work as a shock absorber and a pressure distributing element and diminish further damage to the wound area.

By using a substantially non-absorbing pressure distributing element this will serve as a barrier to the wound exudate as well as the properties of the element will not change due to absorption of wound exudate.

The dressing according to the present invention reduces the impacts from pressure shocks to the selected body part, and offers pressure distributing properties of susceptible areas. These properties are important both in the prophylactic phase as well as in the treatment of an ulcer or protection of the former wound site after healing. The absorbent element of the dressing of the invention is preferably more compressible than the pressure distributing element covering the area next to the treated areas and in that way reducing the direct pressure on the wound.

The combination of an absorbent element combined with an pressure distributing element ensures that no changes in properties of the dressing due to long term pressure is observed. The dressing of the invention can be in the form of a very flexible, thin device of a size rendering it suitable for wearing in shoes without discomfort.

The principles of pressure distributing is to transfer a (too) high pressure from a high risk area to a larger area, preferably an area located proximal or bilateral to the threatened area.

This is often achieved by drawing a ring of pressure distributing material with the high risk area in the centre. However, by isolating the high risk area behind a heavy barrier of pressure distributing material, the high risk area will be locked up inside the ring, giving rise to problems with the circulation of body fluids as well as a risk of developing oedemas. By placing the pressure distributing material apart from the centre of the device, e.g. with the shape of a horseshoe maybe with the legs of the shoe connected by a thin piece of pressure distributing material, around the high risk area, a more open structure is achieved. The central piece of the horseshoe may preferably be in the end being first exposed to the pressure, e.g. if the dressing is worn on the heel, in the heel end, while the open end of the horseshoe is pointing towards the toes. In this way, the construction of the dressing may even enhance the circulation in the tissue of the high risk area.

In one embodiment of the invention the dressing may be substantially planar with circular or elliptical shape for use on e.g. heels. The absorbent element may preferably be situated at the periphery of the dressing.

In another embodiment of the invention the dressing may be in the form of a three-dimensional structure e.g. for use on toes.

The pressure distributing element is preferably an elastomer.

The pressure distributing element may comprise synthetic polymers such as silicones, polyurethanes, elastomeric copolymers or hydrophobic foams with designed properties or it may be a natural polymer such as natural rubbers.

The elastomer has great ability of distributing both the static pressure and the sudden impacts, and at the same time it is durable and does not collapse during use, but conserves its elasticity and shape.

Some elastomers are transparent, which may be an advantage when used in a dressing according to the invention. A transparent or semi-transparent dressing will render it possible to watch the condition of the underlying skin or wound without removing the dressing.

In a preferred embodiment of the invention a water permeable elastomer is used, enabling water vapour transport through the dressing.

Foams are often used as pressure distributing materials. However, many foams may absorb liquid and change properties, by softening or even collapse.

It is preferred that the pressure distributing material does not significantly change pressure distributing properties when contacted with moisture or aqueous liquids, such as wound exudate and perspiration.

However, it may be advantageous to have a pressure distributing material being able to handle minor amounts of moisture. This can be achieved by incorporating an absorber in particular form in the pressure redistributing material.

In one embodiment of the invention the pressure distributing material comprises one or more indentations. The indentations may be in the form of holes, dots, ribs or the like. The presence of the indentations will provide more flexibility to the dressing and, depending on the depths of the indentations they may also serve as diffusion points. The indentations may penetrate the pressure distributing material but not the top layer, if such is present.

Incorporation of a support material in the bandage may be advantageous. It may be in the form of a web or net, e.g. a non-woven or a nylon net. The support material may e.g. be situated at the proximal side of the dressing.

The product may be used both as an ulcer prophylaxis and as a wound dressing for all kinds of pressure ulcers, such as foot ulcers, leg ulcers, hip ulcers and sacrum ulcers. The dressing may also be used as a protection of recently healed and thus still fragile skin.

The absorbent element may comprise a hydrophilic foam, such as polyurethane, silicone, styrene-butadiene, styrene-isoprene or a surface coated polyethylene, or a water soluble or gelling biopolymers such as polysaccharides, e.g. alginates, polyvinyl-pyrrilidone gels or hydrocolloids.

Preferably the absorbent element is more compressible than the pressure distributing element.

The absorbent element may be located as discrete or connected zones in the pressure distributing element, either penetrating the pressure distributing element from top side to the skin-contacting side of the element or only going partly through the dressing, with the open end towards the skin.

The absorbent element may be in the form of a pattern of interconnected zones.

The zones of the absorbent element may be of any shape, e.g. in the form of dots, lines, squares or concentric circles.

The absorbent element is preferably situated eccentrically with respect to the pressure distributing element.

In an embodiment of the invention the absorbent element may comprise more than one absorber, e.g. a foam part in the portion in contact with the skin, and on top of the foam a super absorber part being capable of soaking the moisture from the foam and in this way remove excess moisture from the skin-contacting part.

It is preferred that the surface of the dressing to be brought in contact with the skin shows adhesive properties.

The device can be fully or partly covered with an adhesive on the skin-facing surface in order to attach the device to the wearers body-part, e.g. the plantar, heel or toes. Alternatively, the adhesive can be located on the non-skin facing side, and in this way attach the device to the innersole of the wearers shoe.

The adhesive may be coated to the surface of the dressing in the form of a pattern, such as dots or lines.

In one embodiment the pressure distributing element has inherent adhesive properties.

The device may be covered on the non-skin-contacting surface with a top layer, e.g. a foam, a non-woven, or a film, such as a polyurethane film. The layer will enhance the strength of the dressing as well as it may serve as a barrier for the wound exudate. Further, the top layer may reduce the friction of the dressing.

In one embodiment of the invention the top layer extends beyond the edge of the pressure distributing element defining a flange around the dressing. The flange may optionally be covered with an adhesive.

The dressing may also comprise a protective cover or release liner. It does not need to have the same contour as the dressing, e.g. a number of dressings may be attached to a larger sheet of protective cover. The protective cover is not present during the use of the dressing of the invention and is therefore not an essential part of the invention.

In one embodiment of the invention the dressing further comprises a pressure indicator. The pressure indicator may be visible from the distal side of the dressing, when in use, said pressure indicator showing a durable change after having been exposed to a pressure above a defined level.

The indicator may be dispersed in an adhesive.

In one embodiment of the invention the indicator is incorporated in a film.

The indicator is preferably capable of producing a colour change. Alternatively, the indicator may create a visible change by changing solubility, and in this way change form e.g. clear to opaque.

In another embodiment of the invention the indicator may be in the form of a pressure indicating film, preferably in the form of a mono- or bilayer film.

The indicator may be in the form of microcapsules. These microcapsules may be coated on the dressing or a film or they may be homogeneously dispersed as discrete particles in a matrix, such as an adhesive, absorbent or pressure distributing element.

The incorporation of a pressure indicator renders it possible for the patient or the health care person, to monitor the points of critical pressure in the area around the wound without removing the dressing.

The pressure indicator may be provided in a form either having gradual pressure indication properties or the indicator may have a critical pressure level, above which the indicator will develop a visual indication.

Furthermore, the dressing of the invention may comprise a "non touch" grip known per se for applying the dressing to the skin without touching the adhesive layer. Such a non-touch grip is not present after application of the dressing.

The dressing according to the invention may comprise wound healing associated indicator(s) such as indicators of pH, partial pressure of $O_2$, temperature, radical mechanisms or biotechnological assays, e.g. indicating formation of collagen.

It is also advantageous that a dressing according to the invention comprises wound healing associated indicator(s) or similar device for treatment or prophylaxis of formation of wounds and/or skin abnormalities.

This opens for a combined medical treatment of the wound and an easy and sterile application of the active ingredients, e.g. by incorporating active ingredients such as a cytochine such as growth hormone or a polypeptide growth factor giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorohexidine, silver salts such as sulphadiazine, silver nitrate, silver acetate, silver lactate, silver sulphate, silver-sodiurn-thiosulphate or silver chloride, zinc or salts thereof, metronidazol, sulpha drugs, and penicillins, tissue-healing enhancing agents, e.g. RGD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, pain relieving agents such as lidocaine or chinchocaine, emollients, retinoids or agents having a cooling effect which is also considered an aspect of the invention.

The invention also relates to the use of a dressing comprising a pressure indicator being visible from the distal side of the dressing, when in use for indicating a critical pressure impact to a body part.

The invention relates further to a method of indicating a critical pressure level to a body part, comprising applying a dressing comprising a pressure indicator being visible from the distal side of the dressing, when in use, and after a period of use, inspecting the dressing and detecting an indication of critical pressure.

DETAILED DESCRIPTION OF THE DRAWINGS

An embodiment of the invention is shown in FIG. 1. In this embodiment, a zone of absorbent material (1) surrounded by a pressure distributing material (2). A pressure indicator may be homogeneously dispersed in the pressure distributing material.

Figure 2:
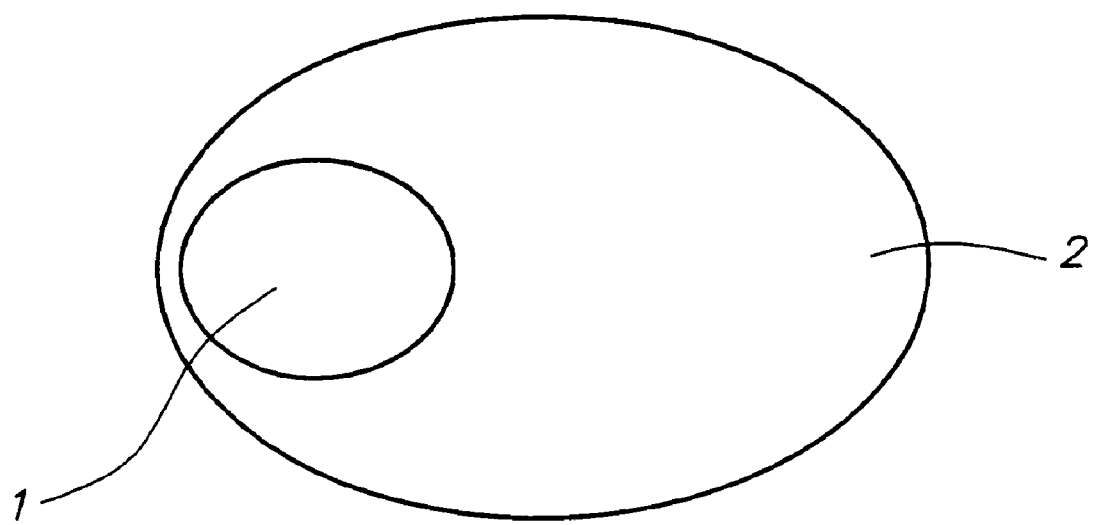
FIG. 2 shows another embodiment of the invention.

In FIG. 2 is shown a preferred embodiment of the invention, with a zone of absorbent material (1) and a pressure distributing element (2). In this embodiment the absorbent material is located near the edge of the dressing. By placing the pressure distributing material here a more open structure is achieved. When applied to the plantar of the foot with the absorbent element pointing towards the toes, the large zone of the pressure distributing element will be the first zone to be exposed to pressure.

Figure 3:
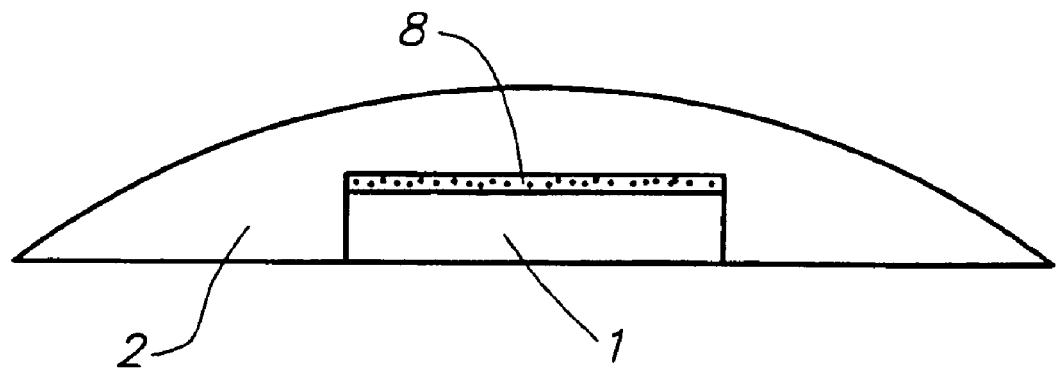
FIG. 3 shows a cross-section of an embodiment of the invention.

In FIG. 3 is shown a cross-section of an embodiment of the invention, with a zone of absorbent element (1) and a pressure distributing element (2). The absorbent element extends partly through the pressure distributing element. On the distal side of the absorbent element is a pressure indicating film (8). The edges of the dressing are bevelled or rounded to enhance the comfort for the user.

Figure 4:
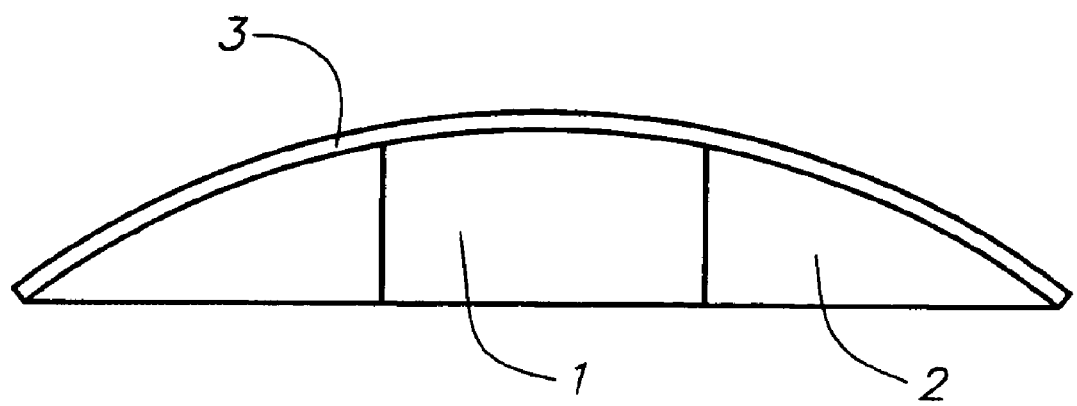
FIG. 4 shows a cross-section of another embodiment of the invention.

In FIG. 4 is shown another embodiment of the invention in which the surface of the dressing not contacted with the skin is covered by a top layer (3). The top layer (3) may enhance the mechanical strength of the dressing. The top layer may be a pressure indicating film. The absorbent element (1) extends through the pressure distributing element (2).

Figure 5:
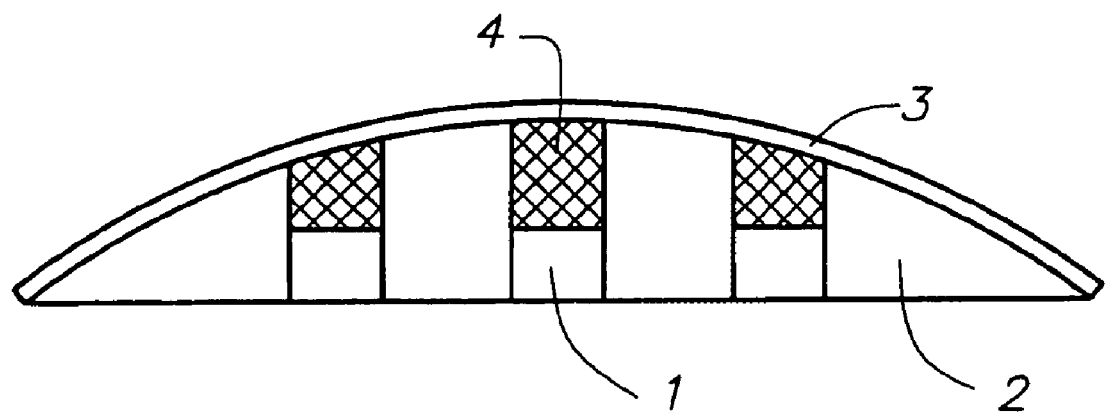
FIG. 5 shows a cross-section of yet another embodiment of the invention.

In FIG. 5 is shown a cross-section of the same embodiment of the invention with one absorbent element (1) at the skin-contacting surface, and on top of the absorbent element is a super absorber (4). A top layer (3) is covering the non-skin-facing surface of the dressing. The top layer may comprise a pressure indicator.

Figure 6:
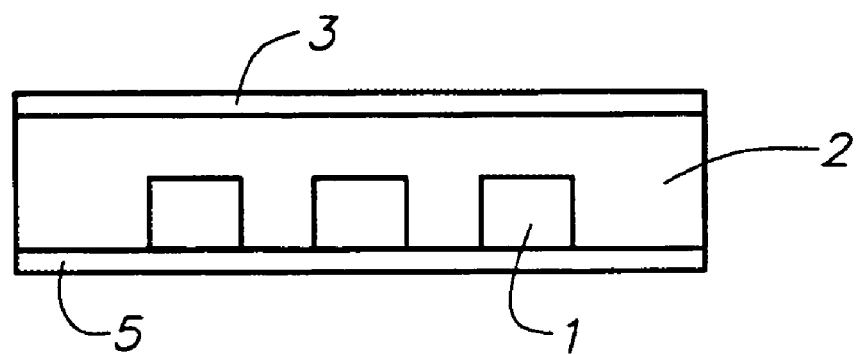
FIG. 6 shows a cross-section of a still further embodiment of the invention.

In FIG. 6 is shown another embodiment of the invention in which the edges are not bevelled, with a top layer (3) on one side and a layer of an adhesive (5) on the skin-facing side. A pressure indicator may be homogeneously dispersed as discrete particles in the adhesive (5).

Figure 7:
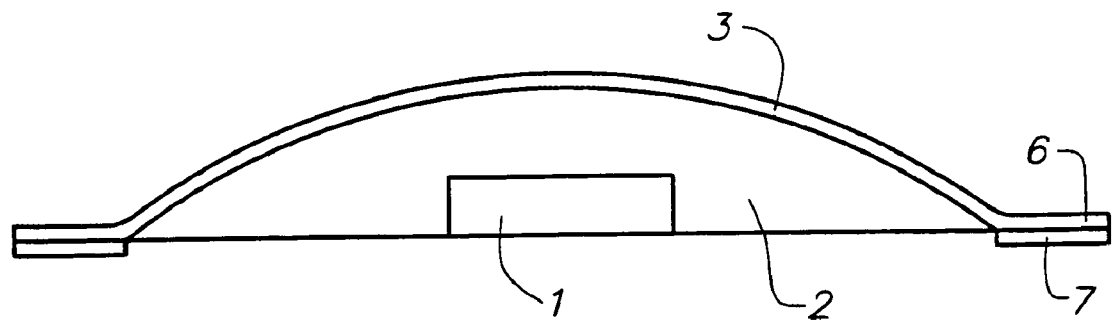
FIG. 7 shows a cross-section of yet another embodiment of the invention.

FIG. 7 is showing an embodiment of the invention in which the top layer (3) is elongated to extend beyond the pressure distributing element (2). On the elongated part of the layer (6) an adhesive (7) is applied, essentially making the concept an island dressing, with an adhesive flange and a non-adhesive centre part. A pressure indicator may be incorporated in the top layer, pressure distributing element or absorbent element.

Figure 8:
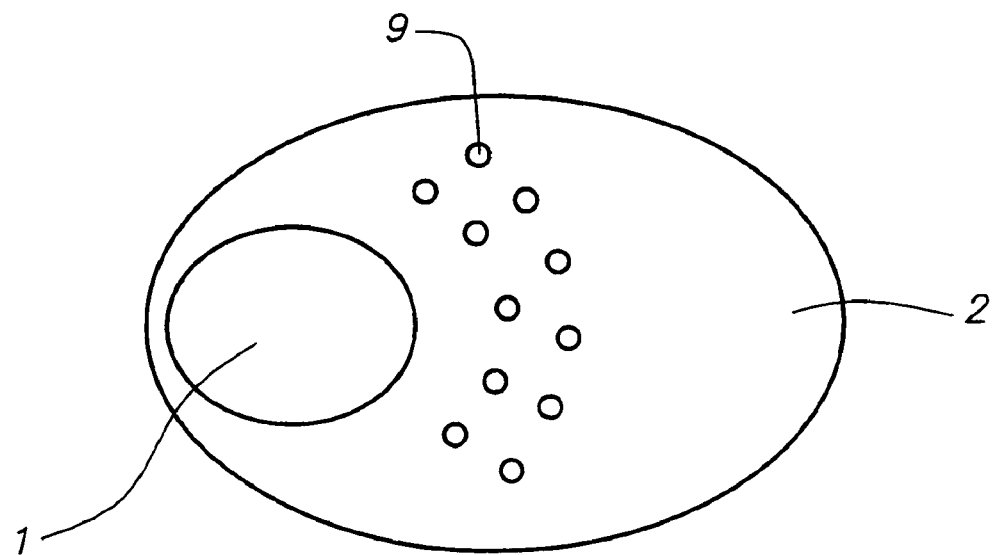
FIG. 8 shows a still further embodiment of the invention seen from above.

In FIG. 8 is shown an embodiment of the invention, with a zone of absorbent material (1) and a pressure distributing element (2). Like in FIG. 2, the absorbent material is located near the edge of the dressing. Indentations (9) in the form of holes or dots are made the pressure distributing element. The presence of the indentations will provide more flexibility to the dressing and, depending on the depths of the indentations they may also serve as diffusion points. The indentations may penetrate the pressure distributing material but not the top layer, if such is present.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A pressure relieving dressing for a wound comprising an absorbent element and a substantially non-absorbing pressure distributing element made of a material that distributes both static pressure and sudden impacts so as to remove pressure from the wound, said absorbent element constituting a part of a proximal skin contacting surface and being encircled by and inset within a thickness of the pressure distributing element which constitutes a remaining part of the surface of the dressing to be in contact with the skin, said absorbent element being situated eccentrically with respect to the pressure distributing element and extending from said skin-contacting surface at least partly through a said thickness of the pressure distributing element.

2. The dressing according to claim 1, wherein the pressure distributing element is an elastomer.

3. The dressing according to claim 2, wherein the elastomer includes a synthetic polymer selected from the group consisting of silicones, polyurethanes, elastomeric copolymers and hydrophobic foams with designed properties or is a natural polymer including natural rubber.

4. The dressing according to claim 1, wherein the absorbent element includes a hydrophilic foam, selected from the group consisting of polyurethane, silicone, styrene-butadiene, styrene-isoprene and a surface coated polyethylene, or water soluble or gelling biopolymers including polysaccharides.

5. The dressing according to claim 1, wherein a surface opposite the skin-contacting surface of the dressing is covered by a top layer.

6. The dressing according to claim 5, wherein the absorbent element extends from said skin-contacting surface substantially completely through the thickness of the pressure distributing element to said top layer.

7. The dressing according to claim 6, wherein said pressure distributing element is generally elliptical in shape and includes one or more indentations that do not extend through said top layer and which provide flexibility to said dressing, said absorbent element being situated adjacent one longitudinal end of said pressure distributing element.

8. The dressing according to claim 7, wherein said indentations are offset from said absorbent element in a longitudinally central portion of said pressure distributing element.

9. The dressing according to claim 5, wherein the pressure distributing material includes one or more indentations that do not extend through said top layer.

10. The dressing according to claim 1, wherein the dressing further comprises a pressure indicator.

11. The dressing according to claim 1, wherein the absorbent element includes a pharmaceutical or antimicrobial agent.

12. The dressing according to claim 1, wherein the surface of the dressing to be brought in contact with the skin shows adhesive properties.

13. The dressing according to claim 1, wherein said pressure distributing element is generally elliptical in shape.

14. The dressing according to claim 13, wherein edges of said dressing are beveled.

15. The dressing according to claim 1, wherein said absorbent element is wholly located to one side of a center line drawn perpendicular to a longitudinal length of said pressure distributing element.

16. The dressing according to claim 1, further comprising an additional absorbent element on top of said skin-contacting absorbent element which has an absorbency greater than that of said skin-contacting absorbent element.

17. The dressing according to claim 1, further comprising a plurality of absorbent elements interspersed with portions of said pressure distributing element and constituting part of the dressing to be in contact with the skin.

18. The dressing according to claim 1, wherein the surface opposite the skin-contacting surface of the dressing is covered by an elongated top layer that extends beyond an outer edge of said pressure distributing element to form a flange.

19. The dressing according to claim 18, wherein adhesive is applied to said flange, said flange encircling said skin-contacting portions of said absorbent element and said pressure distributing element which are non-adhesive.

20. A pressure relieving dressing for a wound comprising an absorbent element constituting a part of a proximal skin-contacting surface, a substantially non-absorbing pressure distributing element constituting a further part of the proximal skin-contacting surface of the dressing and being made of a material that distributes both static pressure and sudden impacts so as to remove pressure from the wound, and an additional absorbent element on top of said skin-contacting absorbent element which has an absorbency greater than that of said skin-contacting absorbent element.

21. A pressure relieving dressing for a wound comprising a substantially non-absorbing pressure distributing element constituting a part of the dressing to be in contact with the skin and being made of a material that distributes both static pressure and sudden impacts so as to remove pressure from the wound, and a plurality of absorbent elements interspersed with portions of said pressure distributing element and constituting a further part of the dressing to be in contact with the skin.

22. A pressure relieving dressing for a wound comprising a substantially non-absorbing pressure distributing element constituting a part of a proximal skin-contacting surface of the dressing and being made of a material that distributes both static pressure and sudden impacts so as to remove pressure from the wound, an absorbent element adjacent one longitudinal end of said pressure distributing element and constituting a further part of the proximal skin-contacting surface, a top layer covering a surface opposite the skin-contacting surface, and a longitudinally central portion of said pressure distributing element having one or more indentations therein that are offset from said absorbent element and that do not extend through said top layer.

23. A pressure relieving dressing for a wound comprising an absorbent element and a substantially non-absorbing pressure distributing element made of a material that distributes both static pressure and sudden impacts so as to remove pressure from the wound, said absorbent element constituting a part of a proximal skin contacting surface and being encircled by and inset within the pressure distributing element which constitutes a remaining part of the surface of the dressing to be in contact with the skin, said absorbent element being situated eccentrically with respect to the pressure distributing element and extending from said skin-contacting surface substantially completely through a thickness of the pressure distributing element.

* * * * *